United States Patent
Bischoff et al.

(12)

(10) Patent No.: US 6,335,199 B1
(45) Date of Patent: Jan. 1, 2002

(54) LIPID COMPOUNDS AND COMPOSITIONS CONTAINING SAME USED FOR THE TRANSFER OF AT LEAST AN ACTIVE SUBSTANCE, IN PARTICULAR A POLYNUCLEOTIDE, IN A TARGET CELL AND THERAPEUTIC USE

(75) Inventors: Rainer Bischoff, Barsebäcksby (SE); Abdesslame Nazih; Yves Cordier, both of Strasbourg (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/171,845

(22) PCT Filed: Feb. 27, 1998

(86) PCT No.: PCT/FR98/00389

§ 371 Date: Oct. 28, 1998

§ 102(e) Date: Oct. 28, 1998

(87) PCT Pub. No.: WO98/37916

PCT Pub. Date: Sep. 3, 1998

(30) Foreign Application Priority Data

Feb. 28, 1997 (FR) .................................................. 97 02420

(51) Int. Cl.$^7$ .................................................. C12N 15/63
(52) U.S. Cl. .................. 435/458; 424/450; 424/460; 424/455; 436/471; 514/2; 514/44
(58) Field of Search .............................. 514/44; 424/450, 424/460; 436/71; 435/455

(56) References Cited

U.S. PATENT DOCUMENTS 6,030,946 A * 2/2000 Klaus et al. .................... 514/12

FOREIGN PATENT DOCUMENTS

| WO | 91 16024 | 10/1991 |
|----|----------|---------|
| WO | 94 05624 | 3/1994 |
| WO | 96 40726 | 12/1996 |
| WO | 97 03939 | 2/1997 |
| WO | 97 31934 | 9/1997 |

OTHER PUBLICATIONS

Sakai et al, "Total synthesis of galantin I. Revision of the original structure", Tetrahedron Letters, vol. 31, No. 22, 1990, pp. 3183–3186, XP002046828.
Czerwinski et al, "total synthesis of edeine D", Journal Of Antiobiotics, vol. 36, No. 8, Aug. 1983, pp. 1001–1006, XP002046829.
Hougard et al (Eur. J. Cell Biol. 44(1): 151–155, see abstract, Aug. 1987.*
Gao et al (Biochemistry 35: 1027–1036, see abstract, Jan. 1996.*
Hanvey et al (Antisense Res. Dev. 1(4): 307–317, 1991.*
Shimogori et al Biochem. Biophys. Res. Comm. 223: 544–548, 1996.*
Verma et al. Nature 389: 239–242 , especially p. 239, Sep. 1997.*
Anderson et al. Nature 392: 25–30, especially pp. 25 and 30.*
Yoshikawa et al FEBS Lett. 396(1): 71–76, ; see especially abstract; p. 71, col. 2, lines 15–21; and p. 76, col. 1, lines 21–22, Aug. 1987.*

* cited by examiner

Primary Examiner—Dave T. Nguyen
Assistant Examiner—Richard Schnizer
(74) Attorney, Agent, or Firm—Burns, Doane, Swecker & Mathis, L.L.P.

(57) ABSTRACT

The present invention relates to lipid compounds of formula I, wherein said compounds are optionally in a cationic form and are optionally combined with one or more biologically acceptable anions. The present invention also relates to complexes comprising at least one cationic lipid compound of the formula I and an active substance comprising negative charges. The present invention further relates to methods of gene therapy using the complexes of the present invention.

41 Claims, 2 Drawing Sheets

LIPID COMPOUNDS AND COMPOSITIONS CONTAINING SAME USED FOR THE TRANSFER OF AT LEAST AN ACTIVE SUBSTANCE, IN PARTICULAR A POLYNUCLEOTIDE, IN A TARGET CELL AND THERAPEUTIC USE

The present invention relates to new lipid compounds and new compositions containing them. More particularly, the present invention relates to the use of said compounds or of said compositions to prepare a vector for transferring an active substance, in particular a therapeutically active substance comprising negative charges, in particular a polynucleotide, into a target cell, particularly a vertebrate cell, and more particularly a mammalian cell.

The transfer of a gene into a given cell is the very basis of gene therapy. This new technology, whose field of application is vast, makes it possible to envisage the treatment of serious diseases for which the conventional therapeutic alternatives are not very effective, or are even nonexistent, and applies to diseases which are either of genetic origin (hemophilia, cystic fibrosis, myopathy and the like) or acquired (cancer, AIDS and the like).

During the past 30 years, numerous tools have been developed which allow the introduction of various heterologous genes into cells, in particular mammalian cells. These different techniques may be divided into two categories. The first category relates to physical techniques such as microinjection, electroporation or particle bombardment which, although effective, are greatly limited to applications in vitro and whose implementation is cumbersome and delicate. The second category involves techniques relating to molecular and cell biology in which the gene to be transferred is combined with a vector of a biological or synthetic nature which promotes the introduction of said material.

Currently, the most effective vectors are viral, in particular adenoviral or retroviral, vectors. The techniques developed are based on the natural properties which these viruses have to cross the cell membranes, to escape degradation of their genetic material and to cause their genome to penetrate into the nucleus. These viruses have already been the subject of numerous studies and some of them are already used experimentally as vectors for genes in humans for the purpose, for example, of a vaccination, an immunotherapy or a therapy intended to make up for a genetic deficiency. However, this viral approach has many limitations, in particular because of the limited capacity for cloning into the viral genome, the risks of spreading in the host organism and in the environment the infectious viral particles produced, the risk of artefactual mutagenesis by insertion into the host cell in the case of retroviral vectors, and the high induction of immune and inflammatory responses in vivo during the therapeutic treatment, considerably limiting the number of administrations which can be envisaged (McCoy et al., 1995, Human Gene Therapy, 6, 1553–1560; Yang et al., 1996, Immunity, 1, 433–442). These numerous disadvantages, in particular in the context of a use in humans, have led several teams to develop alternative systems of transferring polynucleotides.

Several nonviral methods are currently available. By way of example, there may be mentioned coprecipitation with calcium phosphate, the use of receptors mimicking viral systems (for a review see Cotten and Wagner, 1993, Current Opinion in Bio-technology, 4, 705–710), or the use of polymers such as polyamidoamine (Haensler and Szoka, 1993, Bioconjugate Chem., 4, 372–379) or of polymer such as those presented in WO 95/24221 describing the use of dendritic polymers, the document WO 96/02655 describing the use of polyethyleneimine, or of polypropyleneimine and the documents U.S. Pat. No. 5,595,897 and FR 2,719,316 describing the use of conjugates of polylysine. Other non-viral techniques are based on the use of liposomes whose value as agent allowing the introduction, into cells, of certain biological macromolecules, such as for example DNA, RNA, proteins or certain pharmaceutically active substances, has been widely described in the literature. To this end, several teams have already proposed the use of cationic lipids which have a high affinity for cell membranes and/or nucleic acids. Indeed, although it has been shown, in the case of nucleic acids, that this type of macromolecule is capable of crossing the plasma membrane of some cells in vivo (WO 90/11092), it is nevertheless the case that the observed transfection efficiency is still highly limited, because of in particular the polyanionic nature of the nucleic acids which prevent their passage across the cell membrane, which itself has a negative net apparent charge. Since 1989 (Felgner et al., Nature, 337, 387–388), cationic lipids have been presented as molecules which are advantageous for promoting the introduction of large anionic molecules, such as nucleic acids, into certain cells. These cationic lipids are capable of complexing anionic molecules, thus tending to neutralize the negative charges on said molecules and to promote their coming close to the cells. Many teams have already developed various cationic lipids. By way of example, there may be mentioned DOTMA (Felgner et al., 1987, PNAS, 84, 7413–7417), DOGS or Transfectam™ (Behr et al., 1989, PNAS, 86, 6982–6986), DMRIE and DORIE (Felgner et al., 1993, Methods 5, 67–75), DC-CHOL (Gao and Huang, 1991, BBRC, 179, 280–285), DOTAP☐ (McLachlan et al., 1995, Gene Therapy, 2,674–622) or Lipofectamine, as well as those described in Patent Applications WO9116024 or WO9514651

More particularly, Patent Application WO-A-9116024 describes cationic lipids of formula:

in which:

R$_1$ and R$_2$ are in particular alkyl or alkenyl radicals;

Y$_1$ and Y$_2$ are radicals —OCH$_2$—, —OC(=O)— or —O—;

R$_3$ and R$_4$ are alkyl or alkenyl radicals;

R$_5$ is an alkylene chain;

R$_6$ is C(=O)—(CH$_2$)$_m$—NH—, a diaminocarboxylic acid or —C(=O)—(CH$_2$)$_m$—NH— bound to said diaminocarboxylic acid;

R$_7$ is H, spermine, spermidine, histone, a protein, an amino acid or a polypeptide.

However, several studies (by way of examples, see Mahato et al., J. Pharm. Sci., 1995, 84, 1267–1271, Thierry et al., 1995, P.N.A.S., 92, 9742–9746) have demonstrated that the efficiency of transferring the anionic macromolecule into cells could vary depending in particular on the interaction between the complexes and the cell membranes, the cell considered, the lipid composition of the cationic compounds, the size of the complexes formed with the anionic molecules and more particularly the ratio between the positive and negative charges on the different components of said complex. The mechanisms which allow in particular the interaction of the complexes with the cell membranes and the transfer of the complexes into the cell are still to a large extent poorly understood and researchers proceed in their studies based on a highly empirical approach. Other factors such as, for example, the formation of the complexes, the stability, the behavior in vivo, or possibly their toxicity make, in addition, the choice of the lipids to priori non-obvious. It is consequently desirable to provide other cationic lipids possibly having improved properties or properties which are different from the cationic lipids already described.

The Applicant has now identified new lipid compounds, which can be provided in cationic form, useful in particular for transferring an active substance, in particular a therapeutically active substance, comprising negative charges, in particular a polynucleotide, into a target cell, whose use may be envisaged in particular in vivo in the context of a gene therapy.

Accordingly, the subject of the present invention is first of all a lipid compound of formula:

R—HN—[—(CH$_2$)$_m$—NR—]$_{n-1}$—(CH$_2$)$_m$—NH—R    I in which:

the R residues are, independently of each other, a hydrogen atom or a group of formula II:

in which:

R$_1$ and R$_2$ are, independently of each other, C$_6$–C$_{23}$ alkyl or alkenyl radicals, which are linear or branched, or radicals —C(=O)—(C$_6$–C$_{23}$) alkyl or —C(=O)—(C$_6$–C$_{23}$) alkenyl, which are linear or branched, aryl radicals, cycloalkyl radicals, fluoroalkyl radicals, polyethylene glycol groups, oxyethylene or oxymethylene groups which are optionally repeated, linear or branched, optionally substituted, p is a positive integer from 1 to 4, n is a positive integer from 1 to 6, m is a positive integer from 1 to 6 which may be different for each motif —(CH$_2$)$_m$, and more particularly for each motif —(CH$_2$)$_m$—NR— when n>1, the number of R groups of formula II being between 1 and 4.

The expression "alkenyl" is understood to mean that the carbon chain may comprise one or more double bond(s) along said chain.

According to a specific case, the invention relates to a compound chosen from the compounds of formulae:

H$_2$N—[—(CH$_2$)$_m$—NH—]$_n$R    III

RNH—[—(CH$_2$)$_m$—NH]$_n$H    IIIa in which:

R is a group of formula II as defined above and

H$_2$N—[—(CH$_2$)$_m$—NR]$_{n-1}$—(CH$_2$)$_m$—NH$_2$    IIIb in which:

R has one of the meanings indicated for the formula I provided that at least one R is a group of formula II and for each of the formulae:

n is a positive integer from 1 to 6, m is a positive integer from 1 to 6 which may be different for each motif —(CH$_2$)$_m$, and more particularly for each motif —(CH$_2$)$_m$—NR— when n>1.

According to a preferred case, the compounds of formula IIIb contain one or two R groups of formula II.

According to preferred embodiments of the invention, the variations presented below, taken in combination with each other or otherwise, will be chosen:

R$_1$ and R$_2$ are, independently of each other, linear —C(=O)-alkyl or linear —C(=O)-alkenyl radicals,

R$_1$ and R$_2$ are, independently of each other, —C(=O)-alkyl or —C(=O)-alkenyl radicals comprising from 12 to 20 carbon atoms, preferably 12, 16 or 18 carbon atoms, when the lipid comprises 1 or 2 R groups of formula II, n is an integer chosen from the numbers 2, 3 or 4, m is an integer chosen from the numbers 2, 3 or 4.

According to a specific case, it is possible to reduce the length of the alkyl or alkenyl chain so that R$_1$ and R$_2$ are radicals having 6 to 10 carbon atoms, but in this case compounds for which the number of R groups of formula II is equal to 2, 3 or 4 will be preferably chosen.

Preferably, the lipids according to the invention are chosen from the group consisting of the compounds of the following formulae:

for which R$_1$ and R$_2$ are identical and are chosen from the stearoyl and oleoyl radicals.

The compounds according to the invention are prepared by reacting a compound of formula:

V

—NH—R$_3$
—NH—R$_4$
—COOH in which:

R$_3$ and R$_4$ are protecting groups, in particular Fmoc (Grandas et al., 1989, Int. Journal pept. prot. Res. vol 33, 386–390), with an amine of formula:

R$_5$NH[(—CH$_2$)$_m$—NR$_5$]$_{n-1}$—(CH$_2$)$_m$NHR$_5$    VI m and n having the same meaning as for the formula I, $R_5$ being a protecting group, in particular t-butoxycarbonyl (BOC) or a hydrogen atom, at least one of the $R_5$ radicals and at most four of the $R_5$ radicals corresponding to the hydrogen atom.

The functional groups N—$R_3$ and —N—$R_4$ are then deprotected so as to bind, by amidation or alkylation, the radicals $R_1$ and $R_2$ in a known manner, in particular by the action of the corresponding —N-hydroxy-succinimide ester.

The compound obtained is deprotected in the presence of trifluoroacetic acid.

The amines of formula VI are prepared in a known manner.

In the case where the compound of formula VI is 1-4-di-boc-spermidine, reference will be made to the examples indicated below in order to know the practical modalities for the synthesis. The processes described are applicable in general to the syntheses of the compounds according to the invention subject to adaptations within the capability of persons skilled in the art.

However, the compounds of the invention cannot be limited to those obtained by the modes of preparation described above.

The compounds according to the invention may, in addition, be substituted. Such substitutions may in particular consist of a labeling molecule (see labeling molecules in U.S. Pat. No. 4,711,955) which makes it possible, for example, to visualize the distribution of the compounds or of the complexes containing them after administration in vitro or in vivo, a cell targeting molecule or an anchoring molecule. The invention consequently also relates to a compound as presented above, conjugated with one or more targeting components, also called ligands of interest, via the intermediacy of at least a) one of the carbon atoms, in particular chosen from those present on the groups $R_1$ and/or $R_2$, or b) one of the secondary or primary nitrogen atoms of the polyamine chain or of the diaminocarboxylic acid. Such components may allow targeting to a specific cell type, facilitate penetration into the cell, lysis of the endosomes or alternatively intracellular transport and are widely described in the literature. They may be, for example, all or part of sugars, peptides (GRP peptide, Gastrin Releasing Peptide, for example), oligonucleotides, lipids, hormones, vitamins, antigens, antibodies, ligands specific for membrane receptors, ligands capable of reacting with an anti-ligand, fusogenic peptides, nuclear localization peptides, or a combination of such compounds. There may be mentioned more particularly the galactosyl residues which make it possible to target the asyaloglycoprotein receptor at the surface of hepatic cells, the fusogenic peptide INF-7 derived from the influenza virus hemagglutinin subunit HA-2 (Plank et al., 1994, J. Biol. Chem. 269, 12918–12924) or a nuclear localization signal derived from the SV40 virus T antigen (Lanford and Butel, 1984, Cell 37, 801–813) or the Epstein Barr virus EBN-1 protein (Ambinder et al., 1991, J. Virol. 65, 1466–1478).

Such conjugates can be easily obtained by techniques widely described in the literature, and more particularly by chemical coupling, in particular using protecting groups such as trifluoroacetyl or Fmoc or Boc, onto the polyamine and more particularly using one or more orthogonal protecting groups such as those described in Protective Groups in Organic Synthesis (p. 309–406, 1991, eds. T. W. Greene, P. G. M. Wuts, Wiley) onto the polyamine or the diaminocarboxylic acid. The selective deprotection of a protecting group then makes it possible to couple the targeting component, and the lipid is then deprotected. It should be stated, however, that the substitution of the nonreactive groups such as the carbon atoms in the CH or $CH_2$ groups will be carried out during synthesis of the compounds of the invention by methods known to a person skilled in the art, whereas the reactive groups, such as the primary or secondary amines, may be the subject of substitutions on the neosynthesized lipids of the invention.

According to an advantageous case of the invention, said compound is in a cationic form, that is to say that it is in a form which is protonated by binding of a proton onto one or more nitrogen atoms present on the polyamine chain. In this case, said cationic lipid is combined with one or more biologically acceptable anions, such as for example the trifluoroacetate, halide, monomethylsulfate, acetate or phosphate, iodide, chloride, or bromide anion and the like. It is also possible to obtain compounds in cationic form by substitution of the amines, for example, with a methyl or ethyl radical, and the like.

According to another aspect, the invention also relates to a composition comprising at least one compound as described above and optionally at least one adjuvant capable of enhancing the formation of the complex between a said compound and an active substance, or of enhancing the function of these complexes toward the cell.

Preferably, such an adjuvant will be a neutral or zwitterionic lipid, such as for example a lipid which is or is derived from a triglyceride, a diglyceride, cholesterol (see for example U.S. Pat. No. 5,438,044), in particular, a neutral or zwitterionic lipid which is or is derived from a phosphatidylethanolamine (PE), phosphatidylcholine, phosphocholine, sphyngomyelin, ceramide or cerebroside. Advantageously, dioleoylphosphatidylethanolamine (DOPE) will be chosen.

The weight ratio between the compound of the invention and the neutral or zwitterionic lipid is generally between 0.1 and 10, it being understood that this ratio may vary depending on the nature of the components considered. Persons skilled in the art have sufficient knowledge to allow these minor adaptations. It is also possible to use a mixture of neutral and/or zwitterionic lipids or alternatively a mixture of cationic lipids and neutral and/or zwitterionic lipids.

The invention relates, in addition, to a complex comprising at least one compound or at least one composition as described above and at least one active substance, in particular a therapeutically active substance, comprising at least one negative charge. According to a variant of the invention, said complex may, in addition, contain one or more cationic amphiphilic agents such as those described in the literature of which examples were provided above.

According to a specific embodiment, said active substance is chosen from nucleic acids and proteins. Preferably, the active substance of the complex according to the invention is a polynucleotide, said compound or said composition then making it possible to enhance the transfecting power of the polynucleotide in a cell.

"Polynucleotide" is understood to designate a DNA and/or RNA fragment which is double-stranded or single-stranded, linear or circular, natural, isolated or synthetic, designating a precise succession of nucleotides, which are modified or otherwise (see by way of example U.S. Pat No. 5,525,711), labeled or otherwise (see for example U.S. Pat. No. 4,711,955 or EP 302175), making it possible to define a fragment or a region of a nucleic acid without size limitation. Polynucleotide is understood to designate in particular a cDNA, a genomic DNA, a plasmid DNA, a messenger RNA, an antisense RNA, a ribozyme, a transfer RNA, a ribosomal RNA or a DNA encoding such RNAs. "Polynucleotide" or "nucleic acid" are synonymous terms in the context of the present application. "Antisense" is understood to designate a nucleic acid having a sequence complementary to a target sequence, for example an mRNA sequence for which it is sought to block the expression by hybridization with the target sequence; "sense" is understood to designate a nucleic acid having a sequence homologous or identical to a target sequence, for example a sequence which binds to a proteinaceous transcription factor and which is involved in the expression of a given gene.

According to a specific embodiment of the invention, said polynucleotide comprises a gene of interest and components allowing the expression of said gene of interest. In this embodiment, said polynucleotide is advantageously in the form of a plasmid. The components allowing expression are all the components allowing the transcription of said DNA fragment into RNA (antisense RNA or mRNA) and the translation of the mRNA into a polypeptide. They are in particular promoter sequences and/or regulatory sequences which are effective in said cell, and optionally the sequences required to allow excretion or expression of said polypeptide at the surface of the target cells. By way of example, there may be mentioned promoters such as the promoters of the viruses RSV, MPSV, SV40, CMV or 7.5k, of the vaccinia virus, the promoters of the gene encoding muscle creatine kinase, actin, or pulmonary surfactant. It is, in addition, possible to choose a promoter sequence specific for a given cell type or which can be activated under defined conditions. The literature provides a large amount of information relating to such promoter sequences. Moreover, said polynucleotide may comprise at least two sequences, which are identical or different, exhibiting a transcriptional promoter activity and/or at least two coding DNA sequences, which are identical or different, situated, relative to each other, contiguously, far apart, in the same direction or in the opposite direction, as long as the transcriptional promoter function or the transcription of said sequences is not affected. Likewise, it is possible to introduce into this type of nucleic acid construct "neutral" nucleic sequences or introns which do not affect transcription and are spliced before the translation step. Such sequences and their uses are described in the literature. Said polynucleotide may also contain sequences required for intracellular transport, for replication and/or for integration. Such sequences are well known to persons skilled in the art. Moreover, the polynucleotides according to the present invention may also be polynucleotides which are modified such that it is not possible for them to become integrated into the genome of the target cell or polynucleotides which are stabilized with the aid of agents such as, for example, spermine.

In the context of the present invention, the polynucleotide may be homologous or heterologous to the target cell. It may be advantageous to use a polynucleotide which encodes all or part of a polypeptide, in particular a polypeptide having a therapeutic or prophylactic activity, and more particularly an immunogenic activity of the cellular or humoral type. The term polypeptide is understood without restriction as to its size or its degree of modification (for example glycosylation). There may be mentioned, by way of examples, the genes encoding an enzyme, a hormone, a cytokine, a membrane receptor, a structural polypeptide, a polypeptide forming a membrane channel, a transport polypeptide, an adhesion molecule, a ligand, a factor for regulation of transcription, of translation, of replication, or of the stabilization of the transcripts, or an antibody, such as for example the gene encoding the CFTR protein, dystrophin, factor VIII or IX, E6/E7 of HPV, MUC1, BRAC1, β-interferon, γ-interferon, interleukin (IL)2, IL-4, IL-6, IL-7, IL-12, tumor necrosis factor (TNF) type alpha, GM-CSF (Granulocyte Macrophage Colony Stimulating Factor), the Herpes Simplex virus type 1 (HSV-1) tk gene, the gene associated with retino-blastoma or p53 or all or part of immunoglobulins, such as the fragments F(ab)$_2$, Fab', Fab or the anti-idiotypes (U.S. Pat. No. 4,699,880). This list is of course not limiting and other genes may be used.

According to a preferred embodiment, the complexes according to the invention are small in size (less than 500 nm, advantageously less than 200 nm and preferably less than 100 nm).

Moreover, the transfection experiments carried out show that advantageously the weight ratio of the lipid compound according to the invention to said polynucleotide is 0.01 to 100. The optimum ratio is between 0.05 and 10.

The invention also relates to a process for preparing the complexes of cationic compounds/anionic active substances, said process being characterized in that one or more lipids in cationic form or a composition according to the invention whose lipid is in cationic form are brought into contact with one or more active substances comprising at least one negative charge and in that said complex is recovered, optionally after a purification step. It also relates to the kits for preparing such complexes comprising one or more lipids or one or more compositions according to the invention.

In a first instance, according to a first variant, one or more cationic compounds are dissolved with an appropriate quantity of solvent or mixture of solvents which are miscible in water, in particular ethanol, dimethylsulfoxide (DMSO), or preferably a 1:1 (v:v) ethanol/DMSO mixture, so as to form lipid aggregates according to a known method described, for example, in Patent Application WO-A-9603977, or according to a second variant, are suspended with an appropriate quantity of a solution of detergent such as an octylglucoside such as n-octyl-β-D-glucopyranoside, or 6-O-(N-heptylcarbomoyl)-methyl-α-D-glucopyranoside.

The suspension may then be placed in a buffer medium and mixed with a solution of active substance comprising negative charges.

In the case where it is desirable that a neutral or zwitterionic lipid is present in the final complex, a film is formed, in the known manner, prior to the dissolution in the solvent which is miscible with water or in the solution of detergent, with a mixture containing a said cationic compound and a said neutral or zwitterionic lipid, such as for example DOPE.

One of the important characteristics of the process consists in the choice of the ratio between the positive charges of the cationic lipid and the negative charges of the active substance.

Without wishing to be limited by a specific ratio, quantities of the different charges will be chosen so that the ratio between the number of positive charges of the compound or of the cationic composition and the number of negative charges of the active substance is between 0.05 and 20, in particular between 0.1 and 15, and preferably between 5 and 10.

This ratio between the number of positive charges of the cationic compound(s) and/or composition(s) and the number of negative charges of said active substance also constitutes an advantageous characteristic of the complex according to the invention.

The calculation to arrive at such a ratio will take into consideration the negative charges carried by the active substance and the quantity of compound necessary to satisfy the ratio indicated above will be adjusted. The quantities and the concentrations for the other components are adjusted according to their respective molar masses and the number of their positive and/or negative charges.

In the case of the second variant, subsequent dialysis may optionally be carried out in order to reduce the detergent and to recover the complexes. The principle of such a method is for example described by Hofland et al. (1996, PNAS 93, p 7305–7309) and in chapter II of the Philippot et al. document (G. Gregoriadis, 81–89, CRC Press 1993).

It has been shown that the first variant leads to excellent results in terms of the size of the complexes obtained.

According to a third variant, one or more cationic compositions or compounds are suspended in a buffer and then the suspension is subjected to sonication until visual homogeneity is obtained. The lipid suspension is then extruded through two microporous membranes under appropriate pressure. The lipid suspension is then mixed with a solution of active substance comprising negative charges. In the case where a neutral lipid is present in the complex, a film of the mixture of cationic lipid and neutral lipid such as DOPE is formed in a known manner prior to the preparation as a suspension. The same remarks relating to the ratio between the positive charges of the cationic lipid and the negative charges of the active substance as those indicated in the first variant are applicable to this third variant. This so-called sonication-extrusion technique is well known in the art.

The characteristics of the complexes formed may be evaluated by several means which make it possible to determine, for example:

the state of complex formation with the active substance, in particular by identification of the free nucleic acids by agarose gel electrophoresis in the case where the substances are nucleic acids, the size of the particles by a quasi-elastic scattering of light, the absence of precipitation over the long term.

The object of the present invention is also the complexes obtained using the processes listed above.

The invention also relates to the use of a compound, of a composition or of a complex according to the invention to transfer at least one active substance, especially a therapeutically active substance, more particularly a nucleic acid, into target cells, in vitro, ex vivo or in vivo, more particularly in vivo.

"Target cells" according to the invention is understood to mean prokaryotic cells, yeast cells and eukaryotic cells, plant cells, human or animal cells, and in particular mammalian cells. Cancer cells should, moreover, be mentioned. In vivo, the invention may be applied at the level of the interstitial or luminal space of tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilages and endothelium. According to an advantageous choice of the invention, the target cell will be a muscle cell, a hematopoietic stem cell or alternatively a cell of the airways, more particularly a tracheal or pulmonary cell, and advantageously a cell of the respiratory epithelium.

The complexes according to the invention can be used as a medicament for curative, preventive or vaccinal purposes. Accordingly, the subject of the invention is also the complexes of the invention as a medicament for curative, preventive or vaccinal purposes. Such complexes may be used in a method of therapeutic treatment which consists in transferring at least one therapeutically active substance, in particular a polynucleotide, into target cells, in particular a mammalian cell, and more precisely a muscle cell, a hematopoietic stem cell, or a cell of the airways, more particularly a tracheal or pulmonary cell, or a cell of the respiratory epithelium.

A compound according to the invention is most particularly advantageous for transferring a nucleic acid into a muscle cell or a pulmonary cell. It is the compound noted pcTG37 (see example).

More widely, the present invention also relates to a process for introducing an active substance comprising negative charges into a cell in particular in vitro, characterized in that cells, in particular cultured on an appropriate medium are brought into contact with a complex cationic compound/active substance comprising at least one negative charge according to the invention, in particular in the form of a suspension of complexes. After a certain incubation time, the cells are washed and recovered. The introduction of the active substance may be checked (optionally after lysis of the cell) by any appropriate means.

The process of introduction is well known per se. The term "introduction" is understood to mean that the active substance comprising negative charges is transferred into the cell and is located, at the end of the process, inside said cell or at the level of the membrane thereof. In the case where the active substance is a nucleic acid, reference will be made more particularly to "transfection". In this case, the verification of the transfection of the nucleic acid can be carried out by any appropriate means, for example by measuring the expression of the gene considered or the concentration of the expressed protein.

The invention relates more particularly to the use of a compound, of a composition or of a complex according to the invention for the preparation of a medicament for curative, preventive or vaccinal purposes, intended for the treatment of the human or animal body, in particular by gene therapy.

According to a first possibility, the medicament may be administered directly in vivo (for example into a muscle, into the lungs by aerosol and the like). It is also possible to adopt the ex vivo approach which consists in collecting cells from the patient (bone marrow stem cells, peripheral blood lymphocytes, muscle cells and the like), transfecting them in vitro according to the present invention and readministering them to the patient.

The complexes according to the invention may be administered by the intramuscular, intratracheal, intranasal, intracerebral, intrapleural, intratumoral, intracardiac, intragastric, intraperitoneal, epidermal, intravenous or intraarterial route by a syringe or by any other equivalent means, systems suitable for the treatment of the airways or of the mucous membranes such as inhalation, instillation or aerosolization. There may also be mentioned the modes of administration by application of a cream, by oral administration or any other means known to the person skilled in the art and applicable to the present invention.

It is also within the scope of the invention to target specific organs or tissues by administration, in particular by the intravenous route, of a complex according to the invention prepared so as to adjust the ratio of the compound or to the composition/therapeutically active substance in said complex, the apparent charge of the complex (see in particular Liu et al., 1997, Gene Therapy, 4, 517–523; Thierry et al., 1995, P.N.A.S., 92, 9742–9746).

The invention also relates to a method of gene therapy consisting in administering to a patient an appropriate quantity of a composition according to the invention. According to the present invention and in the context of gene therapy in vivo, it is possible to repeat several times, in a given patient, the method as proposed without any major immune reaction being elicited against one of the compounds administered. The administration may take place in a single dose or repeated once or several times after a certain time interval. The repeated administration would make it possible to reduce the quantity of therapeutically active substance, more particularly of DNA, to be administered for a given dose. The appropriate route of administration and dosage vary according to various parameters, for example the individual or disease to be treated or alternatively the polynucleotide to be transferred.

The invention relates more particularly to a pharmaceutical preparation comprising at least one complex as described above, optionally containing, in addition, at least one adjuvant capable of stabilizing said pharmaceutical preparation for the purpose of its storage for example and/or of enhancing the transfecting power of said complex. Such an adjuvant could, for example, be chosen from the group consisting of chloroquine, a protic polar compound chosen in particular from propylene glycol, polyethylene glycol, glycerol, ethanol, 1-methyl-L-2-pyrrolidone or derivatives thereof, or an aprotic polar compound chosen in particular from dimethyl sulfoxide (DMSO), diethyl sulfoxide, di-n-propyl sulfoxide, dimethyl sulfone, sulfolane, dimethylformamide, dimethylacetamide, tetramethylurea, acetonitrile or derivatives thereof. Likewise, said preparation may contain a pharmaceutically acceptable carrier allowing its administration to humans or animals.

In the context of the use of a method of treatment in vivo according to the present invention, it is, in addition, possible to carry out, before the administration of a pharmaceutical preparation as described above, a treatment of the patient designed to observe a temporary depletion of the macrophages making it possible to enhance the transfection rate. Such a technique is described in the literature; see in particular Van Rooijen et al., 1997, TibTech, 15, 178–184.

Finally, the invention relates to a cell transfected with a complex as defined above, particularly a prokaryotic cell, a yeast cell or eukaryotic cell, especially an animal cell, in particular a mammalian cell, and more particularly a cancer cell. According to a preferred case of the invention, said cell is a cell of the airways, more particularly a tracheal or pulmonary cell, and advantageously a cell of the respiratory epithelium.

the examples below illustrate the invention without limiting it in any manner.

EXAMPLES

Figure 1:
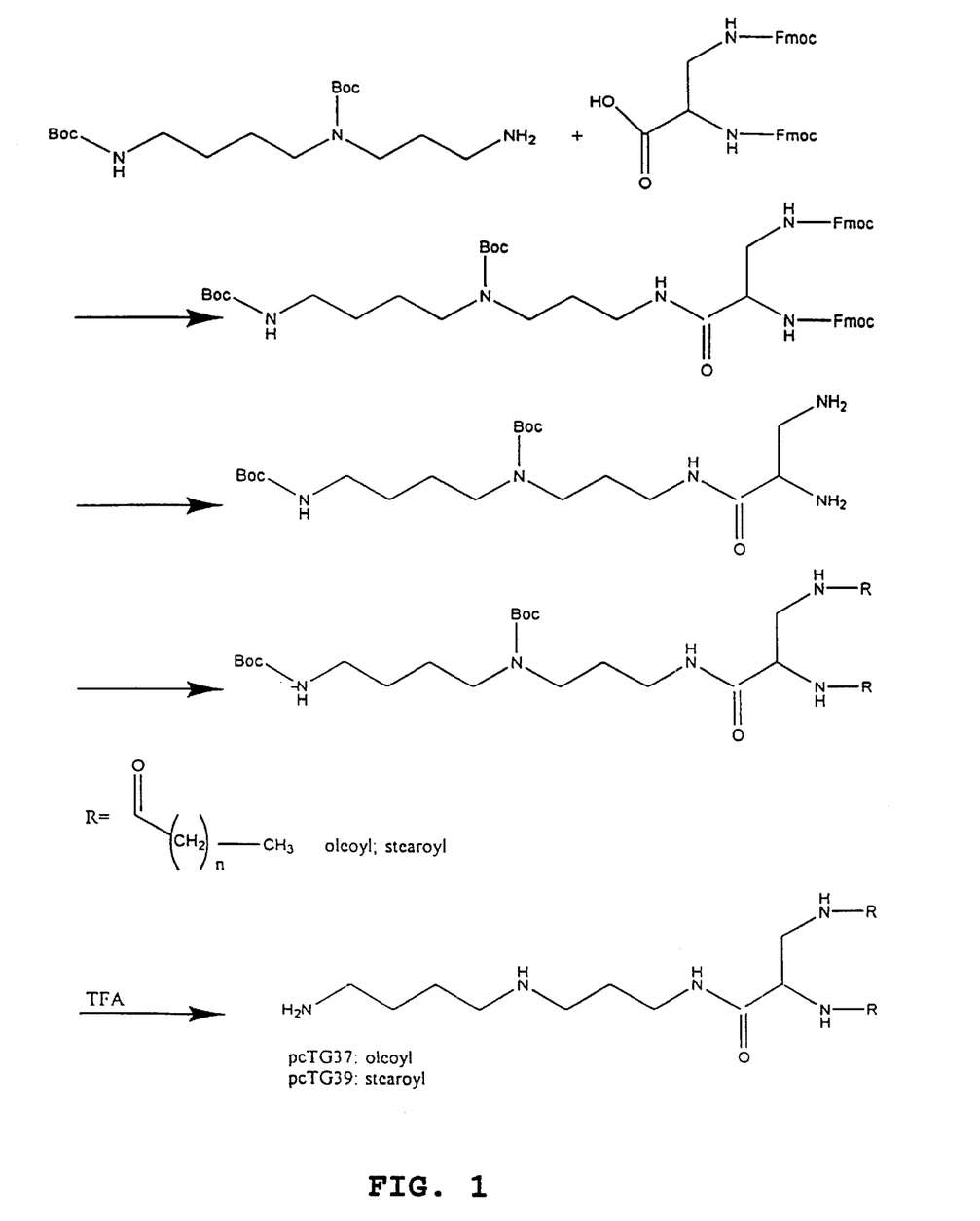
FIG. 1. A diagram of the synthesis of a cationic lipid having the formula I.

The preparation of the cationic lipid of formula I in which $R_1$ and $R_2$, which are identical, are oleoyl or stearoyl radicals, n=2; mα=3, mβ=4 is described below with reference to the diagram of synthesis represented in FIG. 1. α and β are the positions of the —$(CH_2)_m$—NH— motifs from the carbonyl. Synthesis of the cationic lipid of formula I in which n=2, mα=3, mβ=4, R=oleoyl (pcTG37) (see FIG. 1) Synthesis of the intermediate 1-4-di-boc-spermidine The protocol applied in order to obtain 1,4-di-boc-spermidine is published by Goodnow et al. (1990, Tetrahedron 46, 3267–3286). In practice, the intermediate N-propionitrile-1,4-diaminobutane is obtained by reacting 37.6 mmol of diaminobutane (Fluka; reference 32790) diluted in 3.8 ml of dichloromethane+2 ml of methanol at 0° C. with 18.8 mmol of acrylonitrile (Fluka; reference 01710) for 1 hour at 20° C. The amino groups of the product of the reaction are protected with 99 mmol of BOC-ON [(2-boc-oxyimino)-2-phenylacetonitrile] (Fluka; reference 15475) in 50 ml of 2/1 $CH_2Cl_2/CH_3OH$ solvent. The protecting reaction is left overnight at room temperature. The solvents are evaporated off and the product is taken up in 75 ml of ethyl acetate for 3 extractions with 75 ml of 1 M NaOH. The organic phase is again extracted with 5% citric acid and then dried and filtered over $Na_2SO_4$ before evaporation to dryness. The step of reducing the nitriles is then carried out in ether at 0° C. in the presence of 20 mmol of LiAlH4 (Sigma; L0260). After 1 hour 30 min, the reaction is stopped by addition of 20 ml of 1 M NaOH at 0° C., with evolution of hydrogen. The mixture is filtered and extracted 3 times with a 20% NaCl solution in water. After drying the ethereal fraction, the product is deposited on a silica column in a 2/1 $CH_2Cl_2/CH_3OH$ solvent and then eluted in a 15/5/1 $CH_2Cl_2/CH_3OH/(C_2H_5)_3N$ solvent. The fractions containing the di-boc-spermidine are determined by thin-layer chromatography.

NMR data: 1H NMR (200 MHz, CDCl3): 1.43–1.48 ppm (s, 18 H, Boc), 1.48–1.72 ppm (m, 6H, NH(Boc)—$CH_2$—$CH_2$—$CH_2$—$CH_2$—N(Boc)—$CH_2$—$CH_2$—$CH_2$—$NH_2$), 2.69 ppm (t, 2H, J=6.7 Hz, —$CH_2$—$\overline{NH_2}$), 3.07–3.25 ppm (m, 6H, NH(Boc)—$CH_2$—$CH_2$—$CH_2$—$CH_2$—N(Boc)—$CH_2$—$CH_2$—$CH_2$—$\overline{NH_2}$), 4.59 ppm (b, 1$\overline{H}$, NH(Boc)).

Quantity synthesized (1.45 g; 5.1 mmol)—27% yield relative to the quantity of acrylonitrile.

Synthesis of pcTG37

140 μmol of N-hydroxybenzotriazole (Sigma; H2006), then 140 μmol of di-boc-spermidine in 1 ml of anhydrous tetrahydrofuran, and finally 180 μmol of dicyclohexylcarbodiimide (Sigma; D3128) diluted in 2 ml $CH_2Cl_2$ are added to 140 μmol of N-α N-β, di-Fmoc-diaminopropionic (Bachem B2265). After 2 hours of reaction, the dicyclohexylurea formed is filtered and the product is purified on a silica column in a 99/1 $CH_2Cl_2/CH_3OH$ solvent. After evaporation, the Fmoc groups are removed from the product in a solution of 20% piperidine, 20% tetrahydrofuran and 60% $CH_2Cl_2$ for 1 hour. After evaporation, another purification is carried out on a silica column in a 1/1 $CH_2C_2/CH_3OH$ solvent. The fractions containing the product are determined by thin-layer chromatography. The product is dried before the last coupling. 510 μmol of the N-hydroxysuccinimide ester of oleic acid (Sigma O 9506) diluted in 5 ml of anhydrous $CH_2Cl_2$ are added to di-boc-spermidine-diaminopropionamide. After evaporation, the product is purified on a silica column (ether/ethyl acetate; 1/1). The final product, taken up in 1 ml of $CH_2Cl_2$, is Boc deprotected in 10 ml of trifluoroacetic acid (Fluka 91699). To remove the trifluoroacetic acid, evaporation is carried out under reduced pressure after dilution in 50 ml of n-hexane.

Overall yield of synthesis: 64% (89 mg; 90 μmol)

$_1$H NMR (200 MHz, $CDCl_3/CD_3OD$: 0.81 ppm (t, j=6.4 Hz, 6H —$CH_3$), 1.22–1.3 ppm (m, 44 H, —$CH_2$—), 1.51 ppm (m, 4 H, —$CH_2$—$CH_2$—CO—NH—), 1.72–1.90 ppm (m, 6 H, $\overline{NH_3^+}$ —$CH_2$—$CH_2$—$CH_2$—$CH_2$—$NH_2^+$ —$CH_2$—$CH_2$—$CH_2$—NH—), 1.92 ppm (m, 8 H, $CH_2$—CH=), 2.07–2.2 ppm (m, 4 H, $CH_2$—CO—NH—), 2.89 ppm (m: 6 H, $NH_3^+$ —$CH_2$—$CH_2$—$CH_2$—$CH_2$—$NH_2^+$ —$CH_2$—$CH_2$—$CH_2$—$\overline{NH}$—), 4.22 ppm (t, 1 $\overline{H}$, NH—CO—$\overline{CHR}$—NH—), 5.27 ppm (m, 4H, —CH=).

Mass spectrometry: measured 759.7 Da (calculated 760.2 Da).

Synthesis of the cationic lipid of formula I in which n=2, mα=3, mβ=4; R=stearoyl (lipid pcTG39)

The compound pcTG39 is prepared in an amount of 140 µmol in the same manner using stearic acid and dicyclohexylcarbodiimide or (benzotriazol-1-yloxy)tripyrrolidinophosphonium hexafluorophosphate (PyBOP) as coupling agent.

Overall yield of synthesis: 22% (30 mg; 30 µmol)

$^1$H NMR (200 MHz, CDCl$_3$/CD$_3$OD/D$_2$O): 0.68 ppm (t, j=6.8 Hz, 6H, —CH$_3$), 1.06 ppm (m, 48 H, —CH$_2$—), 1.37 ppm (m, 4 H, —CH$_2$—CH$_2$—CO—NH—), 1.53–1.75 ppm (m, 6 H, NH$_3$$^+$—$\overline{CH_2}$—CH$_2$—CH$_2$—CH$_2$—NH$_2$$^+$—CH$_2$—CH$_2$—CH$_2$—NH—), 1.90–2.30 ppm (m, 4 H, CH$_2$—CO—$\overline{NH}$=), 2.74 ppm (m, 6H, NH$_3$$^+$—CH$_2$—CH$_2$—CH$_2$—CH$_2$—NH$_2$$^+$—CH$_2$—CH$_2$—CH$_2$—$\overline{NH}$—), 3.25–3.55 ppm $\overline{(m, 4\ H,}$ —CH$_2$—NH—CO—).

Mass spectrometry: measured 764.5 Da (calculated 764.3 Da).

Preparation of the lipid-DNA complexes by suspension in ethanol

1. Preparation of lipid pcTG37 (and optionally DOPE)/DNA complexes.

The quantities of lipids are calculated based on the concentration of final DNA (0.1 mg/ml for the tests in vitro), the desired charge ratio, the molar mass and the number of positive charges of the chosen cationic lipid. To obtain a complex between pcTG37/DOPE and the plasmid DNA in a ratio of 10 between positive charges provided by the cationic lipid and negative charges provided by the DNA at a final DNA concentration of 0.1 mg/ml, the different ingredients are mixed according to the following calculation:

0.1 mg of DNA/ml, that is to say (0.1/330) mmol of negative charges (330 Da is the average molecular weight of a nucleotide) per ml correspond to 0.30 µmol/ml of negative charges. To obtain 10 times more positive charges, a concentration of 3.0 µmol/ml of positive charges provided by the cationic lipid is required. The molar mass of pcTG37 in trifluoroacetate form is 988 g/mol and the molecule contains 2 positive charges. Therefore, 1.5 µmol/ml of pcTG37 is required, which corresponds to 1.49 mg/ml.

To obtain an equimolar concentration of L-α-dioleoylphosphatidylethanolamine (DOPE, 744 g/mol, Sigma; P0510), 1.12 mg/ml is required in the lipid preparation. The quantities and the concentrations for the other compounds are adjusted according to their respective molar masses and the number of their positive charges.

The lipids are taken up in chloroform, dried by evaporation and then solubilized in chloroform/methanol (v:v) and again dried. The cationic lipids are weighed and the quantity of DOPE is added from a stock solution of 10 or 20 mg/ml in chloroform to a glass tube sterilized with alcohol and with UV in order to obtain a cationic lipid concentration of 2 mM. The solvents are evaporated under vacuum (0.2×10$^5$ Pa (200 mbar)) for 45 min at 45° C. using a vortex of 40 revolutions per minute (Labconco, Rapidvap, Uniequip, Martinsried, Germany). The lipid film is taken up in ethanol so as to be at the cationic lipid concentration of 50 mg/ml.

pcTG37/DOPE 1.49 mg+1.12 mg=2.61 mg in 30 µl of ethanol. This solution is adjusted to 270 µl with 20 mM HEPES pH 7.5 (adjusted with NaOH) in order to prepare a solution at 5 mg/ml final.

The plasmid DNA is prepared from a stock solution at 1 mg/ml (10 mM Tris, 1 mM EDTA, pH 7.5).

For a solution of 0.5 ml final, 50 µl of the stock solution (50 µg DNA) are collected to which 300 µl of 20 mM HEPES pH 7.5 are added.

To complex the DNA with the lipid preparations, the lipids are added to the DNA. The suspension is mixed by aspiration/discharge using a pipette (10 times). The complexes are stored at +4° C.

150 µl of pcTG37/DOPE are added to 350 µl of the DNA solution in order to obtain 0.5 ml of complex at 0.1 mg/ml DNA and a charge ratio of 10.

The preparation of the complexes is carried out under a laminar flow cabinet.

The complexes are obtained whose characteristics are indicated in Table 1 below.

2. Preparation of lipid pcTG39 (and optionally DOPE)/DNA complexes.

The complexes are obtained according to the same protocol as above.

Preparation of the lipid-DNA complexes by suspension in a detergent solution

1. Preparation of lipid pcTG37 (and optionally DOPE)/DNA complexes.

The quantities of lipids are calculated as described above based on the concentration of final DNA (0.1 mg/ml for the tests in vitro), the desired charge ratio, the molar mass and the number of positive charges of the cationic lipid chosen. The lipids are mixed in a glass tube, sterilized with alcohol and with UV, in order to obtain a 2 mM cationic lipid solution (see above). The solvents are evaporated and the lipid film is taken up in a solution of n-octyl, β-D-glucopyranoside (octylglucoside, Sigma, O 9882) according to a cationic lipid/detergent ratio of 1:5 (mol:mol).

375 µl of a 20 mM octylglucoside solution in 20 mM HEPES pH 7.5 are collected and used to take up the film of pcTG37/DOPE lipid mixture. The plasmid DNA is prepared from a stock solution of plasmid DNA at 1 mg/ml of which 50 µl are removed for a final volume of 0.5 ml (0.1 mg/ml final) to which 262.5 µl of 20 mM HEPES pH 7.5 are added. 187.5 µl of the lipid suspension are added to the DNA by aspirating and discharging 10 times using a pipette in order to obtain the final suspension at 0.1 mg/ml of DNA and a +/− charge ratio of 10. To remove the detergent, a dialysis of 3 times 4 hours at room temperature against 20 mM HEPES pH 7.5 is carried out in dialysis microbags (cut-off of 13.2 kD; Sartorius, Göttingen, Germany). The dialyzed DNA/lipid complexes are stored at +4° C. The preparation is carried out in a laminar flow cabinet.

The complexes are obtained whose characteristics are indicated in Table 1 below.

2. Preparation of lipid pcTG39 (and optionally DOPE)/DNA complexes

Based on the same protocol, the complexes whose characteristics are indicated in Table 1 below are obtained.

Preparation of the lipid-DNA complexes by sonication extrusion

The quantities of lipids are calculated as described above based on the concentration of final DNA (0.1 mg/ml for the tests in vitro), the desired charge ratio, the molar mass and the number of positive charges of the cationic lipid chosen. The lipids are mixed in a glass tube, sterilized with alcohol and with UV, in order to obtain a 2 mM cationic lipid solution, as indicated above. The solvents are evaporated and the lipid film is taken up in 900 µl of 20 mM HEPES pH 7.5 at 4° C. for about 16 h. The suspension is sonicated in a sonication bath (Bransonic 221) to visual homogeneity. The lipid suspension is extruded through two membranes with a pore diameter of 0.2 µm (Nucleopore, Costar, Cambridge, Mass., USA) and rinsed with 20 mM HEPES pH 7.5 (extruder from Lipex Biomembranes, Vancouver, Canada) at a maximum pressure of 50 bars. The lipid suspension is kept at room temperature for 1 hour. 450 µl of the lipid suspension are added to 50 µl of a stock solution of plasmid DNA (1 mg/ml) and mixed by aspirating/discharging 10 times using a pipette. The lipid/DNA complexes are stored at +4° C. The preparations are carried out under a laminar flow cabinet.

Protocol for evaluation of the complexing of the DNA by the lipids

A 1% (w:v) agarose gel is prepared in a TAE buffer (TAE: Tris 4.86 g/l+sodium acetate 0.68 g/l+EDTA 0.336 g/l pH 7.8. If necessary, the sample is diluted in TAE and then the sample buffer 0.083% bromophenol blue, 0.083% cyanol xylene FF, 10% glycerol in water) is added so as to have 50 ng DNA/µl. The sample is briefly subjected to a vortex and left for 30 min at room temperature. As a control, the non-complexed plasmid prepared at the same concentration is used. 10 µl (500 ng of DNA) are deposited on the gel and the migration is carried out at 60 mV for 3 hours. The gel is developed in TAE containing 0.006% (v:v) of ethidium bromide at 10 mg/ml for at least 30 min. Next, the gel is rinsed in TAE and analyzed under UV.

Protocol for measuring the size of the particles by quasi-elastic scattering of light The analyses are carried out on a Coulter N4Plus (Coultronics France S.A., Margency, France) at 25° C. after equilibration of the sample for 20 min. An aliquot of the sample is aspirated and discharged several times before being pipetted. The sample is diluted in the measuring tank and homogenized. The measurement of the light diffracted at 90° is carried out for 180 sec after a 180 sec wait. The range used goes from 3 nm to 10 000 nm using 31 bins. To be valid, the sample should give between 50,000 and 1,000,000 counts/sec.

Physicochemical characteristics

The three methods of formulation "injection of ethanol", "dialysis of detergent" and "sonication/extrusion" are applied to the cationic lipids according to the invention with or without equimolar quantities of DOPE at charge ratios of about 10, or 5. The formulations are considered to be appropriate when the DNA is completely complexed (no migration in the agarose gel) and when the complexes have diameters, determined by quasi-elastic scattering of light, less than 500 nm. The table 1 summarizes the results of these analyses. All the DNA/lipid complexes indicated in the table complex the DNA completely.

TABLE 1

| Lipid | Ratio[1] | Size (nm)[2] | Formulation |
| --- | --- | --- | --- |
| pcTG37 | 10 | 77 | ethanol |
| pcTG37 | 5 | 80 | ethanol |
| pcTG37/DOPE | 10 | 79 | ethanol |
| pcTG37/DOPE | 5 | 64 | ethanol |
| pcTG37 | 10 | 240 | detergent |
| pcTG37 | 5 | 59 | detergent |
| pcTG37/DOPE | 10 | 312 | detergent |
| pcTG39/DOPE | 10 | 312 | detergent |
| pcTG37/DOPE | 5 | 280 | sonication |

TABLE 1-continued

| Lipid | Ratio[1] | Size (nm)[2] | Formulation |
| --- | --- | --- | --- |

[1]Ratio between the positive charges of the cationic lipid and the negative charges of the DNA.
[2]The populations which represent less than 10% of the intensity are not indicated. The size is determined 24–48 hours after the preparation.

These analyses show that the formulations meet the necessary requirements. The "injection of ethanol" method gives the best results, the different preparations tested being less than 100 nm in size. The method by dialysis of detergent or sonication/extrusion also makes it possible to obtain complexes meeting the criteria of the present invention.

In vitro transfection of satellite cells

Cultures of dog muscle and human muscle [lacuna] are carried out in an HamF 14 medium (Life Technologies) supplemented with 10% fetal calf serum (FCS, Hyclone, Logan, Utah), 10 µg/ml of insulin (Sigma), 10 ng/ml of EGF (Sigma) and of FGF (Pepro Tech Inc., Rocky Hill, N.J.) 2 mM of glutamine (bioMérieux), and 40 µg/ml of gentamycin (Schering Plough).

The cells are inoculated 24 h to 48 h before the transfection into a 96-well culture plate with about $5 \times 10^3$ to $10^4$ cells per well, at about 30% confluence, and kept at 37° C. under a 5% $CO_2$ and 95% air atmosphere.

The transfections are carried out with mixtures of variable quantities of lipids and plasmid DNA in order to determine the charge ratios and the optimum DNA concentrations per well.

The complexes used are prepared 24 h to 48 h before the transfection and diluted in HamF 14 medium containing 40 µg/ml of gentamycin and 2 mM glutamine.

After removing the culture medium, 100 µl of transfection mixtures with or without 10% FCS are transferred into each of the wells and the plates are incubated for 4 h at 37° C.

All the transfection media are then adjusted to 10% FCS, 10 µg/ml of insulin (Sigma), 10 ng/ml of EGF (Sigma) and of FGF (Pepro Tech Inc., Rocky Hill, N.J.), 2 mM glutamine (bioMérieux), and 40 µg/ml of gentamycin (Schering Plough) for a final volume of 250 µl. The cultures are incubated for 48 h and then the cells are recovered and tested for their capacity to express the luciferase gene. The protein concentrations are determined by the system for testing quantity of protein (Promega).

Transfection of A549 cells with lipid complexes

The A549 cells (epithelial cells derived from human pulmonary carcinoma) are cultured in Dulbecco's modified Eagle's medium (DMEM) containing 10% fetal calf serum (Gibco BRL) 24 hours before the start of the transfection in 96-well plates ($2 \times 10^4$ cells per well) in a humid atmosphere at 37° C. and 5% $CO_2$/95% air. For the transfection in the absence of serum, the medium is removed and replaced with serum-free medium. In another microplate, the following suspensions of lipid/DNA complexes are prepared (lipid/DNA complexes at 0.1 mg/ml of DNA and at the indicated charge ratio): 44 µl (4.4 µg DNA), 22 µl (2.2 µg DNA), 5.5 µl (0.55 µg DNA) of stock solution in the first 3 wells, and 11 µl (0.11 µg DNA) of the stock solution diluted 10-fold in the next well. The volume is adjusted to 110 µl with DMEM and 100 µl are transferred over the A549 cells. The incubation is carried out with 4, 2, 0.5 and 0.1 µg of DNA per well for 4 hours. 50 µl of DMEM+30% fetal calf serum are added 4 hours after the start of transfection and then 100 µl of DMEM+10% FCS 24 hours after the start of transfection. The transfections in the presence of 10% fetal calf serum are carried out in an identical manner except that the transfection occurs in medium with serum.

Analysis of the transfection 48 h after the transfection, the medium is removed and the cells are washed with 100 µl of PBS phosphate solution and lyzed with 50 µl of lysis buffer (Promega). The lysates are frozen at −80° C. until the luciferase activity is measured. The latter is carried out on 20 µl of mixture for one minute using the Luciferase" determination system (Promega) (LB96P Berthold luminometer) in 96-well plates in kinetic mode.

Transfection in vitro

The preparations of cationic lipids pcTG37 were evaluated in transfection in vitro using the A549 cells and the dog primary myoblasts.

The results are summarized in Table 2 below and show the relative light units (RLU) per well. The values given are obtained with 0.5 µg of DNA per well. All the complexes are prepared using the injection of ethanol method. The total protein concentration per well is determined by the conventional techniques (BCA test, Pierce). As a guide, a well contains about 20 to 30 µg of protein.

TABLE 2

| Lipid | Ratio[1] | A549[2] | A549 + serum | myoblasts | myo-blast + serum |
|---|---|---|---|---|---|
| pcTG37 | 10 | $1.7 \times 10^6$ ($4.0 \times 10_8$ RLU/mg/min) | $3.2 \times 10_4$ | 0 | $1.2 \times 10^5$ |
| pcTG37 | 5 | $9.9 \times 10^6$ ($1.4 \times 10_9$ RLU/mg/min) | $3.9 \times 10^3$ | $8.5 \times 10^7$ | $8.6 \times 10^3$ |
| pcTG37/ DOPE | 10 | $3.5 \times 10^6$ | $1.2 \times 10^6$ | $1.5 \times 10^4$ | $4.9 \times 10^5$ |
| pcTG37/ DOPE | 5 | $5.0 \times 10^4$ | $6.7 \times 10^6$ | $1.9 \times 10^6$ | $4.9 \times 10^4$ |

[1]Ratio between the positive charges of the cationic lipid and the negative charges of the DNA.
[2]Free DNA between 0 and 270 relative light units.

Another mode of synthesis of the compounds according to the invention has been developed 1. Synthesis of the polyamine part 1.1. In order to be able to synthesize the "T-branched" compounds for which the group R of formula II is bound to the secondary amines, an N,N'-di-boc-spermine was synthesized. The protocol applied in order to obtain the 1,4-diboc-spermidine is published by Goodnow et al. (1990, Tetrahedron 46, 3267–3286).

The intermediate N-N'-(di-boc)-N,N'-(dipropio-nitrile)-1, 4-diaminobutane is obtained by reacting 37.6 mmol of diaminobutane (Fluka; reference 32790) diluted in 3.8 ml of dichloromethane+2 ml of methanol at 0° C. with 75.2 mmol of acrylonitrile (Fluka; reference 01710), for 1 hour at 0° C. The product of the reaction is blocked with 100 mmol of BOC-ON [(2-boc-oxyimino)-2-phenylacetonitrile] (Fluka; reference 15475) in 50 ml of 2/1 CH$_2$Cl$_2$/CH$_3$OH solvent. The blocking reaction is placed overnight at room temperature. The solvents are evaporated and the product is taken up in 200 ml of ethyl acetate and then subjected to 3 extractions with 200 ml of 1 M NaOH. The organic phase is again extracted with 5% citric acid, dried and filtered over Na$_2$SO$_4$ before evaporation to dryness. A step of reducing the nitrites is then carried out in ether at 0° C. in the presence of 260 mmol of LiAlH4 (Sigma; L0260). After 15 hours, the reaction is stopped by addition of 100 ml of 1 M sodium hydroxide at 0° C., with evolution of hydrogen. The mixture is filtered and extracted three times with a 20% NaCl solution. After drying the ethereal fraction, the product is deposited on a silica column in a 1/1 CH$_2$Cl$_2$/CH$_3$OH solvent and then eluted in a 15/5/1 CH$_2$Cl$_2$/CH$_3$OH/(C$_2$H$_5$)$_3$N solvent. The fractions containing the di-boc-spermine are determined by thin-layer chromatography. Weighing of the final product: 2.45 g (5.8 mmol). Overall yield: 15.5%.

1.2. Synthesis of N,N'-di-boc-spermidine from spermidine. 20 mmol of spermidine (Sigma S2626) diluted in 20 ml of dichloromethane added to 20 ml of methanol, 11 mmol (2 ml) of diisopropylethylamine at 0° C. and 40 mmol of BOC-O-BOC [di-(tert-butyl)-dicarbonate] (Fluka; reference 34660) in 80 ml of 1/1 CH$_2$Cl$_2$/CH$_3$OH solvent. The blocking reaction is placed overnight at room temperature. The solvents are evaporated and then the product is deposited on a silica column and eluted in steps of 9/1 to 8/2 CH$_2$Cl$_2$/CH$_3$OH solvents. The fractions containing the N,N'-di-boc-spermidine are determined by RP-HPLC chromatography. A pure portion of N,N'-di-boc-spermidine is thus isolated from the other position isomers of di-boc-spermidine. Weighing of the final product: 0.58 g (1.68 mmol) Overall yield: 8.5%.

1.3. New process for the synthesis of 1-4-di-boc-spermidine: 50 mmol of diaminobutane (Fluka; reference 32790) diluted in 50 ml of dichloromethane are added to 20 ml of methanol at 0° C. with 58 mmol of acrylonitrile (Fluka; reference 01710) and placed for 1 hour at 0° C. The product of the reaction is blocked with 109 mmol of BOC-ON [(2-boc-oxyimino)-2-phenylacetonitrile] (Fluka; reference 15475) in 50 ml of 2/1 CH$_2$Cl$_2$/CH$_3$OH solvent. The blocking reaction is placed overnight at room temperature. The solvents are evaporated and the product is taken up in 300 ml of ethyl acetate for 3 extractions with 300 ml of 1 M NaOH. The organic phase is again extracted with 5% citric acid, dried and filtered over Na$_2$SO$_4$ before evaporation to dryness. The step of reduction of the nitriles is then carried out in ether at 0° C. in the presence of 140 mmol of LiAlH4 (Sigma; L0260). After 15 hours, the reaction is stopped by addition of 100 ml of 1 M sodium hydroxide at 0° C., with evolution of hydrogen. The mixture is filtered and extracted three times with a 20% NaCl solution. After drying the ethereal fraction, the product is ready to be deposited on a silica column for the final purification.

2. Synthesis of the hydrophobic part

Synthesis of N-a-N-β-di[oleylamido]propionic acid. 9.04 mmol (3.43 g) of the N-hydroxysuccinimide ester of oleic acid (Sigma O 9506) diluted in 10 ml of dioxane are added to 4.1 mmol (0.58 g) of N-a-N-β-diaminopropionic acid, HCl (Bachem F3040) in a mixture of 22 ml of water, 44 ml of dioxane and 20.5 mmol (2.65 ml) of diisopropylethylamine. After 2 hours of reaction, 2 extractions with ether/HCl 5% are carried out, followed by saturated NaCl washing and drying over Na$_2$SO$_4$ before evaporating the ethereal fraction to dryness. The product is deposited on a silica column in a 95/5 CH$_2$Cl$_2$/CH$_3$OH solvent, and then eluted in steps of 95/5, then 92.5/7.5, and finally 90/10 CH$_2$Cl$_2$/CH$_3$OH solvents. The fractions containing n-α-N-β-di[oleyl-amido]propionic acid are determined by thin-layer chromatography. Control on TLC (CH2Cl2/CH3OH 90/10) and NMR. Drying. Weighing: 0.916 g (1.45 mmol), yield: 35.4%.

Synthesis of N-α-N-β-di[laurylamido]propionic acid. 2.2 mmol (0.65 g) of the N-hydroxysuccinimide ester of lauric acid (Sigma L3900) diluted in 10 ml of dioxane are added to 1 mmol (0.14 g of N-β-N-β-diaminopropionic acid, HCl (Bachem F3040) in a mixture of 10 ml of water, 20 ml of dioxane and 5 mmol (0.65 ml) of diisopropylethylamine. The same purification protocol (see N-α-N-β-di[oleylamido]-propionic acid) is applied. Weighing: 0.4 g (0.5 mmol), yield: 50%.

Synthesis of N-α-N-β-di[palmitylamido]propionic acid. 2.2 mmol (0.79 g) of the N-hydroxysuccinimide ester of palmitic acid (Sigma P1162) diluted in 10 ml of dioxane are added to 1 mmol (0.14 g) of N-α-N-β-diaminopropionic acid, HCl (Bachem F3040) in a mixture of 10 ml of water, 20 ml of dioxane and 5 mmol (0.65 ml) of diisopropylethylamine. The activated ester precipitates upon the addition and the reaction takes place in a heterogeneous phase for 15 hours, with stirring, at room temperature. And the same purification protocol (see N-α-N-β-di[oleylamido]-propionic acid) is applied. Weighing: 0.14 g (0.15 mmol), yield: 15%.

3. New synthesis of pcTG37

1.45 mmol 916 mg of N-α-N-β-di[oleylamido]-propionic acid, 1.74 mmol (235 mg) of N-hydroxybenzo-triazole (Sigma; H2006), 2 mmol (265 μl) of diisopropylethylamine, and finally 2.175 mmol (449 mg) of dicyclohexylcarbodiimide (Sigma; D3128) diluted in 10 ml of CHCl$_3$ are added to 1.45 mmol (500 mg) of 1,4-di-boc-spermidine diluted in 30 ml of anhydrous CHCl$_3$. After 2 hours of reaction, the medium is filtered and after evaporation, rediluted in 50/50 ether/hexane, and another filtration-evaporation is carried out. This product is purified on a silica column deposited in ether and eluted in steps of ether/ethyl acetate solvent: 75/25, 50/50, 25/75 and 100% ethyl acetate. Control on TLC (ethyl acetate) and NMR. The final product, taken up in 10 ml of CH$_2$Cl$_2$, is Boc deprotected by adding dropwise at 0° C. 50 ml of trifluoroacetic acid (Fluka 91699) redistilled at 72° C. and diluted in 50 ml of CH$_2$Cl$_2$. After 4 hours, the medium is evaporated twice at reduced pressure after dilution in 50 ml of n-hexane. The product is taken up in 10 ml of ether, precipitated in hexane and filtered on filter paper. The product is taken up by washing the paper in a 1/1 CH$_2$Cl$_2$/CH$_3$OH solvent. Controls on TLC (ethyl acetate), HPLC and NMR. Evaporation and weighing: 670 mg (0.68 mmol) yield: 47%.

4. Synthesis of pcTG89 (equivalent of pcTG37 but in a T-branched form)

The same protocol is applied as for pcTG37 but by replacing 1,4-di-boc-spermidine with N,N'-di-boc-spermidine. Weighing of the protected product: 170 mg (0.18 mmol), yield: 12.2%.

Intravenous injection of complexes according to the invention

Figure 2:
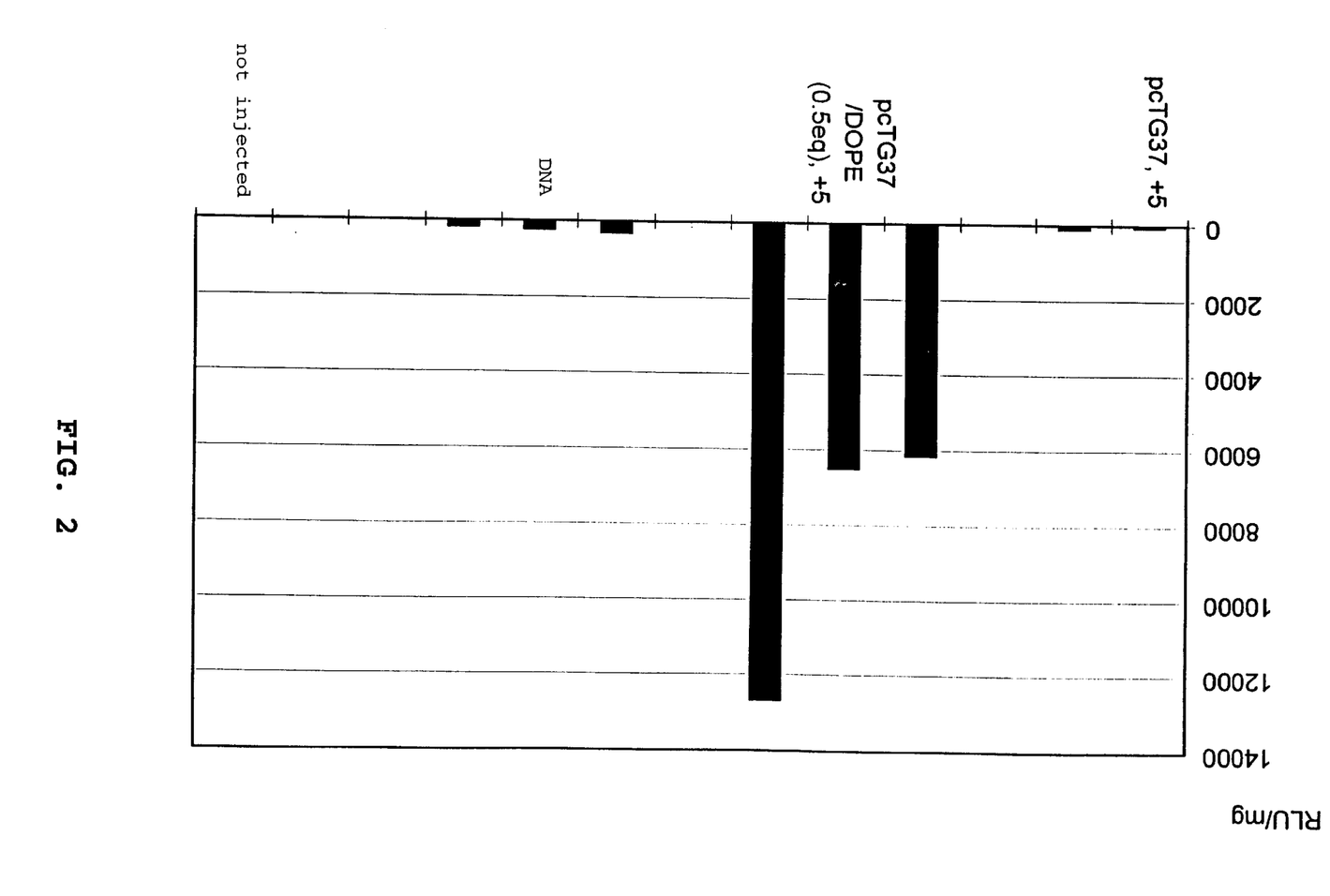
FIG. 2. Luciferase activity obtained in vivo after intravenous injection of a complex of the present invention, containing the lipid pcTG337, in the presence or absence of DOPE, and a plasmid containing the gene for luciferase pTG11o33.

The results are summarized in FIG. 2. Complexes according to the invention were synthesized according to the methods described above from the compound pcTG337, in the presence or in the absence of DOPE (2:1, mol:mol), at a fixed charge ratio of 5, using a plasmid containing the gene for luciferase pTG11033 (French Patent Application No. 97/08267).

The mice used are 9- to 11-week-old C57BL/6 female mice. One day before the injection with the complex according to the invention, the mice are pretreated by injecting 50 μl of a preparation of chlodronate encapsulated in a liposome (see Van Rooijen and Sanders, 1994, J. Immunol. Methods, 174, 83–93) incorporated in a total volume of 200 μl (+150 μl of PBS buffer). The intravenous injections are carried out into the tail after disinfecting the skin with 70% ethanol. The volume injected is 250 μl and the quantity of DNA is 60 μg, the quantity of lipid is 345 μg.

Two days after the injections, the mice are sacrificed. After extraction, the tissues are frozen in liquid nitrogen and stored at −80° C. To measure the luciferase activity, the tissues are mechanically ground with the aid of a pestle in a mortar placed on dry ice. 500 μl of a lysis buffer (Promega) are added to the tissue debris obtained from the lungs and subjected to three freeze/thaw steps. The cellular debris is removed by centrifugation and the luciferase activity (in RLU/min, relative light unit per minute) is measured on 20 μl of supernatant in accordance with the manufacturer's instructions (Promega) by adding 100 μl of reagent and by measuring the activity by luminescence. The luciferase activity measured is standardized relative to the protein quantity with the aid of a calibration series prepared by commercially available luciferase (Promega). The total protein quantity is, moreover, determined by the bicinchoninic acid BCA calorimetric method (Smith et al., 1985, Anal. Biochem., 150, 76–85 Pierce) using an aliquot of supernatant. This makes it possible to express the luciferase activity in RLU per milligram of protein extracted from the tissues. Controls are carried out for which the mice were not injected or were injected with DNA alone (60 μg) in a 20 mM HEPES buffer pH 7.5. The results (FIG. 2) show that the expression of the luciferase reporter gene in the lungs after intravenous injection of complexes containing the compound according to the invention at a charge ratio of 5, in the presence of DOPE is markedly enhanced relative to the injection of DNA alone. The values indicated are the mean values obtained from 3 mice injected.

What is claimed is:

1. A lipid compound of formula:

$$Ra\!-\!HN\!-\!\![-\!(CH_2)m_1\!-\!NR_b\!-\!]_{n-1}\!-\!(CH_2)m_2\!-\!NH\!-\!R_c \quad\quad I$$

wherein:

the $R_a$, $R_b$ and $R_c$ residues are, independently of each other, a hydrogen atom or a group of formula II:

wherein:

$R_1$ and $R_2$ are, independently of each other, $C_6$–$C_{23}$ alkyl or alkenyl radicals, which are linear or branched, or radicals —C(=O)—($C_6$–$C_{23}$) alkyl or —C(=O)—($C_6$–$C_{23}$) alkenyl, which are linear or branched, aryl radicals, cycloalkyl radicals, fluoroalkyl radicals, polyethylene glycol groups, oxyethylene or oxymethylene groups, with the proviso that when either $R_1$ or $R_2$ is a polyethylene glycol group, an oxyethylene or an oxymethylene group, the other is a linear or branched $C_6$–$C_{23}$ alkyl or alkenyl radical, a linear or branched —C(=O)—($C_6$–$C_{23}$) alkyl or —C(=O)—($C_6$–$C_{23}$) alkenyl radical, an aryl radical, a cycloalkyl radical, a fluoroalkyl radical, p is a positive integer from 1 to 4, n is a positive integer from 1 to 6, $m_1$ and $m_2$ are a positive integer from 1 to 6, and $m_1$ may be different for each motif —$(CH_2)m_1$—$NR_b$, and wherein the total number of groups of formula II in said compound of formula I is between 1 and 4.

2. The compound of claim 1 wherein $R_a$ and $R_b$ are a hydrogen atom, $R_c$ is group of formula II as defined in claim 1, n is a positive integer from 1 to 6, $m_1$ and $m_2$ are a positive integer from 1 to 6, and $m_1$ may be different for each motif —$(CH_2)m_1$—$NR_b$.

3. The compound of claim 1 wherein $R_b$ and $R_c$ are a hydrogen atom;

$R_a$ is group of formula II as defined in claim 1, n is a positive integer from 1 to 6, $m_1$ and $m_2$ are a positive integer from 1 to 6, and m1 may be different for each motif —$(CH_2)m_1$—$NR_b$.

4. The compound of claim 1 wherein $R_a$ and $R_c$ are an hydrogen atom, $R_b$ is as defined in claim 1 provided that at least one of the $R_b$ group in the n−1 repeats is of formula II, n is a positive integer from 1 to 6, $m_1$ and $m_2$ are a positive integer from 1 to 6, and $m_1$ may be different for each motif —$(CH_2)m_1$—$NR_b$.

5. The compound of claim 4, wherein it contains one or two $R_b$ groups of formula II.

6. The compound of claim 1, wherein $R_1$ and $R_2$ are, independently of each other, linear —C(=O)-alkyl or linear —C(=O)-alkenyl radicals.

7. The compound of claim 1, wherein $R_1$ and $R_2$ are linear $C_{12}$–$C_{20}$ alkyl or alkenyl radicals, linear —C(=O)—($C_{12}$–$C_{20}$) alkyl or linear —C(=O)—($C_{12}$–$C_{20}$) alkenyl radicals, and wherein said compound comprises 1 or 2 groups of formula II.

8. The compound of claim 1, wherein $R_1$ and $R_2$ are linear alkyl, linear alkenyl radicals, linear —C(=O)-alkyl or linear —C(=O)-alkenyl of 12, 16 or 18 carbon atoms.

9. The compound of claim 1, wherein n is 2, 3 or 4.

10. The compound of claim 1, wherein $m_1$ and $m_2$, are independently of each other 2, 3 or 4.

11. The compound of claim 1, wherein $R_a$ and $R_b$ are each a hydrogen atom, $m_1$ is 4, $m_2$ is 3, n is 2, $R_c$ is of formula II wherein, p is 1 and $R_1$ and $R_2$ are identical and are —C(=O)—($C_6$–$C_{23}$) alkyl or —C(=O)—($C_6$–$C_{23}$) alkenyl radicals.

12. The compound of claim 1, wherein $R_a$ and $R_b$ are each a hydrogen atom, $m_1$ is 4, $m_2$ is 3, n is 2, $R_c$ is of formula II wherein, p is 1 and $R_1$ and $R_2$ are identical and are chosen from the stearoyl or oleoyl radicals.

13. The compound of claim 1, wherein $R_a$ and $R_c$ are each a hydrogen atom, $m_1$ is 4, $m_2$ is 3, n is 2, $R_b$ is of formula II wherein, p is 1 and $R_1$ and $R_2$ are identical and are —C(=O)—($C_6$–$C_{23}$) alkyl or —C(=O)—($C_6$–$C_{23}$) alkenyl radicals.

14. The compound of claim 1, wherein $R_a$ and $R_c$ are each a hydrogen atom, $m_1$ is 4, $m_2$ is 3, n is 2, $R_b$ is of formula II wherein, p is 1 and $R_1$ and $R_2$ are identical and are chosen from a stearoyl or oleoyl radical.

15. The compound of claim 1, wherein it is conjugated with one or more ligands via one of the secondary or primary nitrogen atoms comprised in formula I or in formula II.

16. A complex comprising at least one compound of claim 1, wherein said compound is a cationic compound, and at least one active substance, comprising at least one negative charge.

17. The complex of claim 16, wherein said active substance is a nucleic acid.

18. The complex of claim 17, wherein said nucleic acid is chosen from the group consisting of a cDNA, a genomic DNA, a plasmid DNA, an antisense polynucleotide, a messenger RNA, a ribosomal RNA, a ribozyme, a transfer RNA, or a DNA encoding such RNAs.

19. The complex of claim 18, wherein said nucleic acid comprises a gene of interest and elements allowing the expression of said gene of interest.

20. The complex of claim 16, having a size of less than 500 nm.

21. The complex of claim 20, having a size of less than 100 nm.

22. The complex of claim 16, wherein the ratio between the number of positive charges of the cationic compounds and the number of negative charges of said active substance varies from 0.05 to 20.

23. A complex comprising at least one compound of claim 1, wherein $R_a$ and $R_b$ are each a hydrogen atom, $m_1$ is 4, $m_2$ is 3, n is 2, $R_c$ is of formula II wherein, p is 1 and $R_1$ and $R_2$ are identical and are —C(=O)—($C_6$–$C_{23}$) alkyl or —C(=O)—($C_6$–$C_{23}$) alkenyl radicals, and said active substance is a nucleic acid.

24. A complex comprising at least one compound of claim 1, wherein $R_a$ and $R_b$ are each a hydrogen atom, $m_1$ is 4, $m_2$ is 3, n is 2, $R_c$ is of formula II wherein, p is 1 and $R_1$ and $R_2$ are identical and are chosen from a stearoyl or oleoyl radical, and said active substance is a nucleic acid.

25. A complex comprising at least one compound of claim 1, wherein $R_a$ and $R_c$ are each a hydrogen atom, $m_1$ is 4, $m_2$ is 3, n is 2, $R_b$ is of formula II wherein, p is 1 and $R_1$ and $R_2$ are identical and are —C(=O)—($C_6$–$C_{23}$) alkyl or —C(=O)—($C_6$–$C_{23}$) alkenyl radicals, and said active substance is a nucleic acid.

26. A complex comprising at least one compound of claim 1, wherein $R_a$ and $R_c$ are each a hydrogen atom, $m_1$ is 4, $m_2$ is 3, n is 2, $R_b$ is of formula II wherein, p is 1 and $R_1$ and $R_2$ are identical and are chosen from a stearoyl or oleoyl radical, and said active substance is a nucleic acid.

27. The complex of claim 16 further comprising at least one adjuvant which enhances the formation of the complex between said compound and said active substance.

28. The complex of claim 27, wherein said adjuvant is a neutral or zwitterionic lipid.

29. The complex of claim 27, wherein said adjuvant is a triglyceride, a diglyceride, cholesterol, a phosphatidylethanolamine (PE), phosphatidylcholine, phosphocholine, shingomyelin, ceramide or cerebroside.

30. The complex of claim 27, wherein said adjuvant is dioleoylphosphatidylethanolamine (DOPE).

31. The complex of claim 27, wherein the ratio between the weight of compound and adjuvant present in the complex is between 0.1 and 10.

32. The complex of claim 27, wherein said active substance is a nucleic acid comprises a gene of interest and elements allowing the expression of said gene of interest.

33. The complex of claim 23, wherein said complex further comprises at least one adjuvant which enhances the formation of the complex between said compound and said active substance.

34. The complex of claim 24, wherein said complex further comprises at least one adjuvant which enhances the formation of the complex between said compound and said active substance.

35. The complex of claim 25, wherein said complex further comprises at least one adjuvant which enhances the formation of the complex between said compound and said active substance.

36. The complex of claim 26, wherein said complex further comprises at least one adjuvant which enhances the formation of the complex between said compound and said active substance.

37. A process for preparing a complex wherein one or more compounds of claim 1 are brought into contact with one or more active substances comprising at least one negative charge and in that said complex is recovered.

38. The process of claim 37, wherein said compounds are dissolved beforehand in a solvent which is miscible with water.

39. The process of claim 37, wherein said compounds are suspended beforehand in a detergent solution.

40. The process of claim 39, wherein it further comprises a step of purification of said complex by dialysis.

41. A process for transferring an active substance comprising at least one negative charge into a cell, wherein said cell is brought into contact with a complex of claim 16.

* * * * *